United States Patent [19]

Rudolph

[11] Patent Number: 4,999,346

[45] Date of Patent: Mar. 12, 1991

[54] NOVEL COMPOSITION AND PROCESS FOR CONTROL OF COCKROACH POPULATION

[75] Inventor: Robin R. Rudolph, Grand Prairie, Tex.

[73] Assignee: Sandoz Ltd., Basle, Switzerland

[21] Appl. No.: 377,376

[22] Filed: Jul. 3, 1989

Related U.S. Application Data

[63] Continuation of Ser. No. 162,936, Mar. 2, 1988, abandoned, which is a continuation-in-part of Ser. No. 884,855, Jul. 14, 1986, abandoned, which is a continuation-in-part of Ser. No. 683,984, Dec. 20, 1984, abandoned, which is a continuation-in-part of Ser. No. 680,676, Dec. 12, 1984, abandoned.

[51] Int. Cl.$^5$ .................... A01N 37/06; A01N 57/00
[52] U.S. Cl. .................................... 514/120; 514/549
[58] Field of Search ................................ 514/120, 549

[56] References Cited

U.S. PATENT DOCUMENTS

| | | | |
|---|---|---|---|
| 3,758,645 | 9/1973 | Leber et al. | 260/941 |
| 4,473,582 | 9/1984 | Greene | 424/304 |

Primary Examiner—Allen J. Robinson
Attorney, Agent, or Firm—Allen E. Norris

[57] ABSTRACT

Insecticidal composition comprising propetamphos and hydroprene is useful for safe, fast, complete and long lasting control of cockroach populations. A method for control of the cockroach population comprises an administration of the novel composition to the locus of the cockroach population. Both hydroprene and propetamphos are administered in an effective, cockroach population controlling amount.

19 Claims, No Drawings

NOVEL COMPOSITION AND PROCESS FOR CONTROL OF COCKROACH POPULATION

This is a continuation of application Ser. No. 162,936, filed Mar. 2, 1988, now abandoned; which in turn is a continuation-in-part of application Ser. No. 884,855, filed July 14, 1986, now abandoned; which in turn is a continuation-in-part of application Ser. No. 683,984, filed Dec. 20, 1984, now abandoned; which in turn is a continuation-in-part of application Ser. No. 680,676, filed Dec. 12, 1984, now abandoned.

BACKGROUND OF THE INVENTION

1. Field of the Invention

This invention concerns highly active insecticidal compositions comprising propetamphos and hydroprene. The novel compositions are useful for control of cockroach populations and/or for prophylactic protection against cockroach infestation.

The current invention is also directed to a process for control of cockroach population which process comprises applying to a locus of the cockroach population, in an effective cockroach population controlling aggregate amount, (a) hydroprene [an insect growth regulator (IGR)], and (b) propetamphos (an insecticide).

2. Background

The cockroach is one of the most difficult insects to control. It is primarily a nocturnal insect which forages in exposed locations at night and finds hidden harborages during the day. The life cycle of the cockroach begins with eggs formed in capsules called ootheca. The eggs first hatch into Stage I nymphs which then progress over about 74 days through five more nymphal Stages II–VI to fully developed adult cockroaches. In her adult life span, the female adult cockroach lives for approximately 144 days and produces six ootheca containing about 40 eggs each. Thus the population growth potential is tremendous. A cockroach population continues to grow in a geometrical fashion as long as the three basic requirements of food, water and harborage are sufficient. Oftentimes, a cockroach population will be found to have stabilized in number because of some limitation in one or more of the three basic requirements.

There are two possible ways to deal with the cockroach infestation. One is to submit the cockroach population to a repeated treatment with insecticide. The second is to submit it to a repeated treatment with IGR which will interfere with cockroach maturation and fertility.

It has been observed that if a stabilized cockroach population is under stress, for example when it is temporarily stressed by application of an insecticide, and the stress is ended (e.g., according to the residual activity of the insecticide), the cockroach population responds to the end of the stress by producing increased numbers of young cockroaches much beyond the previously stabilized population level. After the residual activity of the insecticide has become ineffective, the cockroach population compensates for loss due to the stress. Such compensation results in an overall population explosion, reaching much higher numbers of cockroaches than the previously stabilized population level. The population explosion occurs whenever the insecticide looses its toxic effect on the cockroaches. That is particularly true in cases when the insecticide does not affect or interfere with the reproductive potential of surviving cockroaches.

The application of insecticide alone thus has an immediate but short-term effect on reducing the cockroach population. Moreover, because the stress on the population is only temporary, eventually such application results in increased cockroach population only a short time after the insecticide residual activity ends. The residual activity of an insecticide effective on a cockroach population generally does not last for more than about eight weeks. In addition, because of the high toxicity of insecticides, it is often necessary and preferable to restrict the number of applications and the areas to which the insecticide is applied to prevent a health hazard to people.

An alternative to treatment with insecticides is to treat the infested area with environmentally safe hydroprene or other IGRs. The drawback of treatment with hydroprene or the other IGRs is the long time period before the effect on cockroaches is observed. Such delay is caused by the IGRs' mode of action. When an IGR is applied to the locus of cockroach infestation the adult cockroaches are not affected at all and the immature nymphs seemingly continue to develop through successive stages to adults. However, if the cockroaches during their nymphal development come into contact with an IGR they become irreversibly morphologically deformed and physiologically unable to reproduce. This effect, together with the excellent residual activity of IGRs, greatly impacts the cockroach population as the viable reproducing individuals begin to decline in number around four to six months after the first application of IGR to the locus of the population. In addition, although unable to reproduce, the cockroaches treated with an IGR develop into adults and compete with other cockroaches for food, water and harborage, thereby further suppressing the cockroach population.

A scaled-up test in a 1000 cubic foot testing chamber simulating a kitchen with a fairly heavy German cockroach infestation has shown that a single application of a 1.2% hydroprene fogger at 250 ml per 100 $m^2$ provides some degree of supression of the cockroach population. However, the complete eradication of cockroaches was never accomplished.

The results obtained in scale-up tests led to a field testing of hydroprene alone or in combination with certain insecticides in actual homes and apartments with current cockroach infestations. Insecticides chosen to test the effect of such a combination on reduction of a cockroach population were DDVP, chlorpyrifos, propoxur and propetamphos. A single application of hydroprene foggers used in conjunction with DDVP or propoxur foggers provided reasonably good control but never complete eradication of the cockroach population in four single family houses and twenty-five apartments. Similarly, the hydroprene treatment alone had shown a definite hydroprene effect, i.e. the presence of anomalous nymph stages, but significant reduction of the cockroach population was never achieved within a four-month testing period.

These trials show that neither the hydroprene alone or any one of the tested insecticides alone was able to achieve safe, fast, complete and long-lasting control of cockroaches. To achieve the above goal, an insecticide was needed which in combination with hydroprene would enhance the morphogenetic action of hydroprene and complement it with its own effect.

RELATED DISCLOSURES

Both active compounds of this invention, propetamphos and hydroprene, are known and disclosed in U.S. Pat. Nos. 3,758,645, 4,021,461 and 4,473,582 and Belgium patent 753,579 as pesticides and insecticides. U.S. Pat. No. 3,758,645 and Belgium patent 753,579 disclose propetamphos as being a useful pesticide against chewing and sucking insects, particularly against spider mites; U.S. Pat. No. 4,021,461 discloses use of juvenile hormones for control of insects; US Pat. No.4,473,582 describes an insecticidal stick applicator for administration of insecticides.

The above cited prior art discloses that propetamphos and hydroprene, individually, have some effect in controlling cockroach populations. The synergism discovered in a particular combination of both, i.e. a superior efficacy of the novel compositions together with fast, safe, complete and long lasting effect of the present invention, is unexpected and could not have been predicted from the individual activities of propetamphos or hydroprene.

SUMMARY

One aspect of this invention concerns the novel composition comprising a mixture of propetamphos, hydroprene and optionally a suitable carrier substance.

Another aspect of this invention concerns the method for control of cockroaches which method comprises applying to the locus of cockroach infestation a composition comprising essentially propetamphos and hydroprene in amount from 52 to 224 mg/m$^2$ of propetamphos and 12 to 50 mg/m$^2$ of (R,S)-hydroprene or 1 to 20 mg/m$^2$ of (S)-hydroprene.

Yet another aspect of this invention concerns a new process for control of a cockroach infestation which process comprises an administration of propetamphos and hydroprene optionally in admixture with a suitable carrier substance to a site of a cockroach infestation.

Another aspect of this invention concerns the prophylactic method for control of cockroaches which method comprises the administration of a composition consisting of propetamphos, hydroprene and optionally a suitable carrier substance to the place where the infestation by cockroaches is the most probable and expected, such as cockroach harborages, cracks and crevices, new buildings or building materials.

DETAILED DESCRIPTION OF THE INVENTION

Definitions

"Propetamphos" as used herein is the common name for (E)-1-methylethyl-3-[[(ethylamino)methoxyphosphinothioyl]oxy]-2-butenoate. The use of propetamphos as an insecticide and the synthesis thereof is described by Leber and Lutz, U.S. Pat. No. 3,758,645 which is hereby incorporated by reference.

"Chlorpyrifos" as used herein is the common name for compound 0,0-diethyl 0-(3,4,6-trichloro-2-pyridinyl) phosphorothioate. The compound and its use are disclosed in U.S. Pat. No. 3,244,586, and the compound is known under the trademark Dursban ®.

"Dichlorvos" as used herein is the common name for 2,2-dichloroethenyl dimethyl phosphate. The compound and its usee are disclosed in U.S. Pat. No. 2,956,073 and the compound is known under the trivial name DDVP and the trademark Vapona ®.

"Propoxur" as used herein is the common name for 2-isopropoxyphenyl methylcarbamate. The compound and its insecticidal use are disclosed in U.S. Pat. No.3,111,539, and the compound is known under the trademark Baygon ®.

"Hydroprene" as used herein is the common name for ethyl(2E,4E)-3,7,11-trimethyl-2,4-dodecadienoate. The use of hydroprene as an IGR and the synthesis thereof is described in U.S. Pat. No. 4,021,461, hereby incorporated by reference. There is an asymmetric carbon atom at the C-7 in hydroprene and, accordingly, there are (R) and (S) enantiomers of the compound. As used herein "(R,S)-hydroprene" refers to the racemic mixture and "(S)-hydroprene" refers to hydroprene comprising the (S)-(+) enantiomer. Where "hydroprene" is used herein without reference to its enantiomeric content, the term is inclusive of both (R,S)-hydroprene and (S)-hydroprene.

An "insect growth regulator" as used herein, is a compound which is effective in regulating the growth and maturation processes of an insect.

The term "locus of the cockroach population" as used herein refers to unit areas such as an apartment, apartment building, restaurant, house, warehouse, theater, office and office building, and the like wherein there exists an infestation of cockroaches which may or may not be a stabilized population of cockroaches.

The term "control of a cockroach population" as used herein means a significant percentage decrease in the number of cockroaches in the tested facility. Controlled cockroach population means the number of cockroaches acceptable to the occupants or users of that particular facility.

The term "spot treatment" as used herein and in the appended claims means that the formulation is applied as a spot or crack and crevice treatment and not to the general space or forage areas.

UTILITY

In accordance with the disclosure made herein, it has been discovered that combined application of the IGR hydroprene and the insecticide propetamphos to the locus of the cockroach population provides a safe, fast, complete, long-lasting and highly effective control of the cockroach population. Surprisingly, the combination of active ingredients hydroprene and propetamphos and their application individually or in admixture to cockroach infested places overcomes the disadvantages (short effect of propetamphos and long delay following the hydroprene treatment) of each active ingredient alone. The application of a combination of both active ingredients to the locus of a cockroach population produces a significantly greater percent reduction than the application of either hydroprene or propetamphos alone, and such reduction is greater than the additive effect of both active compounds when used separately. Thus, the application of propetamphos and hydroprene shows a surprisingly greatly increased result.

Propetamphos, an organophosphate insecticide, is toxic to cockroaches dermally and orally at all stages of their morphogenetic cycle including the adult stage. It possesses moderate to good residual activity (ca. 60 days). The mode of action of propetamphos is cholinesterase inhibition.

The application of propetamphos alone to cockroach infested apartments results in immediate (within one month) reduction of cockroaches by approximately 50–60%. The level of activity reaches its peak at approximately 60 days wherein the reduction in number of cockroaches reaches approximately 80%. After 60 days, there is a gradual erosion of efficacy and at 120 days (4 months) the infestation may be back to 64–50% depending on the climate and other surrounding conditions.

IGRs generally have very small, if any, immediate toxic effect on cockroaches. On the contrary, an initial application of IGR does, by providing a foreign but non-toxic stress, actually increase the cockroach population. Because of their excellent residual activity and mode of action, the application of IGRs may eventually cause substantial decrease in the cockroach population but such decrease occurs only over a period of several months.

Hydroprene itself, while a highly active IGR that mimics the function of the insect juvenile hormone, has no insecticidal activity or direct toxicity to the insect at any of the morphogenetic stages. Thus, the application of hydroprene to a population of cockroaches has no immediate, short term beneficial effect. The adult insects remain unaffected and immature insects although morphogenetically inferior still continue to develop to an infertile adult. However, because hydroprene interferes with the hormonal balance of the immature cockroach, it eventually leads to the infertile adult population and to the otherwise deformed (wrinkled wings, darkened cuticle) insect. Infertility together with bodily deformations adversely affects the cockroach population which as a consequence begins to show a decline in numbers about six months after the hydroprene treatment.

Moreover, probably due to the initial stress, for the first four months, the application of hydroprene alone results in an approximate 60–70% increase of cockroaches. Only after four months does this level gradually decrease.

The novelty of this invention lies in the fact that while the propetamphos alone applied to cockroach-infested places reduces cockroach infestation only to approximately 60% for four months and while the hydroprene alone during the same interval does not in fact result in reduction of the number of cockroaches (just the opposite, it actually increases the number of cockroaches by approximately 56%), the combination of the two decreases the cockroach population by as much as 80–90% during the same interval, showing thus 20–30% greater decrease than the additive effect can account for.

A mixture of propetamphos and hydroprene, unexpectedly and surprisingly, produces a significantly greater percent reduction of cockroach population (up to 88% decrease) than either treatment alone (propetamphos up to 61% decrease, hydroprene up to 56% increase) and far greater than the actual additive effect of the components used separately (5% decrease).

The expected results of the use of propetamphos in admixture with hydroprene for treatment of a cockroach infestation would be either to cancel each other's effect and to reach a post-treatment count approximately equal to or only about 5% lower than the pre-treatment count. In the best case, when the effect of hydroprene is completely discounted, the decrease in the cockroach population could be only 50–60% as observed after administration of propetamphos alone.

Instead, the application of mixture of propetamphos with hydroprene reduces the cockroach population approximately 88% in the same four-month period. This reduction is far superior to that seen after application of either active compound alone. The resulting reduction is greater than would be expected from the additive effect of both components and indicates the synergism of the mixture of propetamphos and hydroprene when used in certain ratio and in certain manner for control of the cockroach population.

In summary, this invention has the following properties unobserved previously:

It increases direct toxic effect of insecticide on cockroaches above that observed previously.

It increases residual activity of the directly toxic active ingredient propetamphos by extending its efficacy beyond its normal duration.

It enhances at the same time the morphogenetic effect of the IGR hydroprene.

It results in a total response greater than the additive effect of both propetamphos and hydroprene used separately.

Administration and Formulation

In practice, both the active ingredients propetamphos and hydroprene may be administered either in admixture or individually in separate steps but in close time sequence so that one treatment follows immediately the other. In the latter case it does not appear to be critical as to whether the hydroprene formulation or the propetamphos formulation is applied first. For convenience and saving of time, it is preferred to apply the spot treatment of propetamphos first and then immediately to apply the general space treatment using a hydroprene aerosol fogger.

Each active ingredient is administered individually as a control treatment for laboratory or field testing.

The hydroprene is always administered in the liquid form. The propetamphos may be applied either in the liquid form or as a solid formulation (wettable powder, granule or dust).

Hydroprene is usually applied to the locus of the cockroach population as a general space treatment. As such, the preferred application is by use of a fogger or an aerosol which provides excellent coverage of general forage areas and harborages of the cockroaches. Hydroprene can also be administered as an emulsifiable concentrate using a suitable sprayer.

Propetamphos is usually applied to the locus of the cockroach population either as a general space treatment or as a spot treatment. For health reasons the spot treatment is preferred. For both treatments, the usual mode of administration is by sprayer, duster or aerosol which permits careful direction of the application of the insecticide. The propetamphos is primarily applied to harborages such as baseboards, storage areas, closets, around water pipes, behind and under cabinets, and similar areas.

(RS)-hydroprene is administered to the site at 12 to 50 mg/m$^2$. Preferably, (RS)-hydroprene is administered to the site at 18 to 36 mg/m$^2$. Most preferably, (RS)-hydroprene is administered to the treatment site at 20 to 30 mg/m$^2$.

If the formulation is an aerosol, volume deliveries can vary from 250 ml to 1,000 ml per 100 m$^2$. Weight:-weight adjustments in the level of (RS)-hydroprene to diluents must be made to achieve the above ranges of application rates.

If the formulation is an emulsifiable concentrate, deliveries can vary from 500 ml to 2,000 ml per 100 m$^2$.

Weight:weight adjustments in the level of (RS)-hydroprene must be made in the final dilution to achieve the above ranges of application rates.

Examples of such adjustment are presented below in Table A.

TABLE A

W:W Formulation Adjustments in (RS) -Hydroprene mg/m$^2$

Aerosols:

*Ranges of (RS) -Hydroprene in mg/m$^2$*

| | | | | |
|---|---|---|---|---|
| 250 ml/100 m$^2$ @ | 0.48% = | 12 to 50 = | 250 ml/100 m$^2$ @ | 2.0% |
| 500 ml/100 m$^2$ @ | 0.24% = | 12 to 50 = | 500 ml/100 m$^2$ @ | 1.0% |
| 750 ml/100 m$^2$ @ | 0.16% = | 12 to 50 = | 750 ml/100 m$^2$ @ | 0.67% |
| 1000 ml/100 m$^2$ @ | 0.12% = | 12 to 50 = | 1000 ml/100 m$^2$ @ | 0.5% |

*Preferred Ranges of (RS) -Hydroprene in mg/m$^2$*

| | | | | |
|---|---|---|---|---|
| 250 ml/100 m$^2$ @ | 0.72% = | 18 to 36 = | 250 ml/100 m$^2$ @ | 1.44% |
| 500 ml/100 m$^2$ @ | 0.36% = | 18 to 36 = | 500 ml/100 m$^2$ @ | 0.72% |
| 750 ml/100 m$^2$ @ | 0.24% = | 18 to 36 = | 750 ml/100 m$^2$ @ | 0.48% |
| 1000 ml/100 m$^2$ @ | 0.18% = | 18 to 36 = | 1000 ml/100 m$^2$ @ | 0.36% |

*Most Preferred Ranges of (RS) -Hydroprene in mg/m$^2$*

| | | | | |
|---|---|---|---|---|
| 250 ml/100 m$^2$ @ | 0.8% = | 20 to 30 = | 250 ml/100 m$^2$ @ | 1.2% |
| 500 ml/100 m$^2$ @ | 0.4% = | 20 to 30 = | 500 ml/100 m$^2$ @ | 0.6% |
| 750 ml/100 m$^2$ @ | 0.27% = | 20 to 30 = | 750 ml/100 m$^2$ @ | 0.4% |
| 1000 ml/100 m$^2$ @ | 0.2% = | 20 to 30 = | 1000 ml/100 m$^2$ @ | 0.3% |

Emulsifiable Concentrates Final Dilution:

*Ranges of (RS) -Hydroprene in mg/m$^2$*

| | | | | |
|---|---|---|---|---|
| 500 ml/100 m$^2$ @ | 0.24% = | 12 to 50 = | 500 ml/100 m$^2$ @ | 1.0% |
| 1000 ml/100 m$^2$ @ | 0.12% = | 12 to 50 = | 1000 ml/100 m$^2$ @ | 0.5% |
| 1500 ml/100 m$^2$ @ | 0.08% = | 12 to 50 = | 1500 ml/100 m$^2$ @ | 0.33% |
| 2000 ml/100 m$^2$ @ | 0.06% = | 12 to 50 = | 2000 ml/100 m$^2$ @ | 0.25% |

*Preferred Ranges of (RS)-Hydroprene in mg/m$^2$*

| | | | | |
|---|---|---|---|---|
| 500 ml/100 m$^2$ @ | 0.36% = | 18 to 36 = | 500 ml/100 m$^2$ @ | 0.72% |
| 1000 ml/100 m$^2$ @ | 0.18% = | 18 to 36 = | 1000 ml/100 m$^2$ @ | 0.36% |
| 1500 ml/100 m$^2$ @ | 0.12% = | 18 to 36 = | 1500 ml/100 m$^2$ @ | 0.24% |
| 2000 ml/100 m$^2$ @ | 0.09% = | 18 to 36 = | 2000 ml/100 m$^2$ @ | 0.18% |

*Most Preferred Ranges of (RS)-Hydroprene in mg/m$^2$*

| | | | | |
|---|---|---|---|---|
| 500 ml/100 m$^2$ @ | 0.4% = | 20 to 30 = | 500 ml/100 m$^2$ @ | 0.6% |
| 1000 ml/100 m$^2$ @ | 0 2% = | 20 to 30 = | 1000 ml/100 m$^2$ @ | 0.3% |
| 1500 ml/100 m$^2$ @ | 0.13% = | 20 to 30 = | 1500 ml/100 m$^2$ @ | 0.2% |
| 2000 ml/100 m$^2$ @ | 0.10% = | 20 to 30 = | 2000 ml/100 m$^2$ @ | 0.15% |

(S)-hydroprene is administered to the site at 1 to 20 mg/m$^2$. Preferably (S)-hydroprene is administered to the site at 2 to 15 mg/m$^2$. Most preferably (S)-hydroprene is administered to the treatment site at 3 to 13 mg/m$^2$.

If the formulation is an aerosol, volume deliveries can vary from 250 ml to 1000 ml per 100 mg/m$^2$. Weight:weight adjustments in the level of (S)-hydroprene to diluents must be made to achieve the above ranges of application rates. Likewise, if the formulation is an emulsifiable concentrate, deliveries may vary from 500 ml to 2000 ml per 100m$^2$. Weight:weight adjustments in the level of (S)-hydroprene must be made in the final dilution to achieve the above ranges of application rates.

Examples of such adjustments are presented below in Table B.

TABLE B

W:W Formulation Adjustments in (S) -Hydroprene mg/m$^2$

Aerosols:

*Ranges of (S) -Hydroprene in mg/m$^2$*

| | | | | |
|---|---|---|---|---|
| 250 ml/100 m$^2$ @ | 0.04% = | 1.0 to 20 = | 250 ml/100 m$^2$ @ | 0.8% |
| 500 ml/100 m$^2$ @ | 0.02% = | 1.0 to 20 = | 500 ml/100 m$^2$ @ | 0.4% |
| 750 ml/100 m$^2$ @ | 0.013% = | 1.0 to 20 = | 750 ml/100 m$^2$ @ | 0.27% |
| 1000 ml/100 m$^2$ @ | 0.01% = | 1.0 to 20 = | 1000 ml/100 m$^2$ @ | 0.20% |

*Preferred Ranges of (S)-Hydroprene in ml/m$^2$*

| | | | | |
|---|---|---|---|---|
| 250 ml/100 m$^2$ @ | 0.8% = | 2 to 15 = | 250 ml/100 m$^2$ @ | 0.6% |
| 500 ml/100 m$^2$ @ | 0.04% = | 2 to 15 = | 500 ml/100 m$^2$ @ | 0.3% |
| 750 ml/100 m$^2$ @ | 0.027% = | 2 to 15 = | 750 ml/100 m$^2$ @ | 0.2% |
| 1000 ml/100 m$^2$ @ | 0.02% = | 2 to 15 = | 1000 ml/100 m$^2$ @ | 0.15% |

*Most Preferred Range of (S)-Hydroprene in mg/m$^2$*

| | | | | |
|---|---|---|---|---|
| 250 ml/100 m$^2$ @ | 0.12% = | 3 to 13 = | 250 ml/100 m$^2$ @ | 0.52% |
| 500 ml/100 m$^2$ @ | 0.06% = | 3 to 13 = | 500 ml/100 m$^2$ @ | 0.26% |
| 750 ml/100 m$^2$ @ | 0.04% = | 3 to 13 = | 750 ml/100 m$^2$ @ | 0.17% |
| 1000 ml/100 m$^2$ @ | 0.03% = | 3 to 13 = | 1000 ml/100 m$^2$ @ | 0.13% |

Emulsifiable Concentrates Final Dilution:

*Ranges of (S)-Hydroprene in mg/m$^2$*

| | | | | |
|---|---|---|---|---|
| 500 ml/100 m$^2$ @ | 0.02% = | 1.0 to 20 = | 500 ml/100 m$^2$ @ | 0.40% |
| 1000 ml/100 m$^2$ @ | 0.01% = | 1.0 to 20 = | 1000 ml/100 m$^2$ @ | 0.20% |

TABLE B-continued

W:W Formulation Adjustments in (S)-Hydroprene
mg/m²

| | | | | |
|---|---|---|---|---|
| 1500 ml/100 m² @ | 0.007% = | 1.0 to 20 = | 1500 ml/100 m² @ | 0.13% |
| 2000 ml/100 m² @ | 0.005% = | 1.0 to 20 = | 2000 ml/100 m² @ | 0.10% |

*Preferred Ranges of (S)-Hydroprene in mg/m²*

| | | | | |
|---|---|---|---|---|
| 500 ml/100 m² @ | 0.04% = | 2 to 15 = | 500 ml/100 m² @ | 0.30% |
| 1000 ml/100 m² @ | 0 02% = | 2 to 15 = | 1000 ml/100 m² @ | 0.15% |
| 1500 ml/100 m² @ | 0.013% = | 2 to 15 = | 1500 ml/100 m² @ | 0.10% |
| 2000 ml/100 m² @ | 0.01% = | 2 to 15 = | 2000 ml/100 m² @ | 0.075% |

*Most Preferred Ranges of (S)-Hydroprene in mg/m²*

| | | | | |
|---|---|---|---|---|
| 500 ml/100 m² @ | 0 06% = | 3 to 13 = | 500 ml/100 m² @ | 0.26% |
| 1000 ml/100 m² @ | 0.03% = | 3 to 13 = | 1000 ml/100 m² @ | 0.13% |
| 1500 ml/100 m² @ | 0.02% = | 3 to 13 = | 1500 ml/100 m² @ | 0.087% |
| 2000 ml/100 m² @ | 0.015% = | 3 to 13 = | 2000 ml/100 m² @ | 0.065% |

Propetamphos is administered to the site at 52 to 224 mg/m². Preferably propetamphos is administered to the site at 76 to 148 mg/m². Most preferably propetamphos is administered to the treatment site at 100 to 124 mg/m².

If the formulation is an aerosol, volume deliveries can vary from 250 ml to 1000 ml per 100m². Weight:weight adjustments in the level of propetamphos to diluents must be made to achieve the above ranges of application rates.

If the formulation is an emulsifiable concentrate, deliveries can vary from 500 ml to 2000 ml per 100m². Weight:weight adjustments in the level of propetamphos must be made in the final dilution to achieve the above ranges of application rates.

Examples of such adjustments are presented below in Table C.

TABLE C

W:W Formulation Adjustments in Propetamphos
mg/m²

Aerosols:

*Ranges of Propetamphos in mg/m²*

| | | | | |
|---|---|---|---|---|
| 250 ml/100 m² @ | 2.1% = | 52 to 224 = | 250 ml/100 m² @ | 8.96% |
| 500 ml/100 m² @ | 1.04% = | 52 to 224 | 500 ml/100 m² @ | 4.48% |
| 750 ml/100 m² @ | 0.69% = | 52 to 224 = | 750 ml/100 m² @ | 2.99% |
| 1000 ml/100 m² @ | 0.52% = | 52 to 224 = | 1000 ml/100 m² @ | 2.24% |

*Preferred Ranges of Propetamphos in mg/m²*

| | | | | |
|---|---|---|---|---|
| 250 ml/100 m² @ | 3.04% = | 76 to 148 = | 250 ml/100 m² @ | 5.92% |
| 500 ml/100 m² @ | 1.52% = | 76 to 148 | 500 ml/100 m² @ | 2.96% |
| 750 ml/100 m² @ | 1.01% = | 76 to 148 = | 750 ml/100 m² @ | 1.97% |
| 1000 ml/100 m² @ | 0.76% = | 76 to 148 | 1000 ml/100 m² @ | 1.48% |

*Most Preferred Ranges of Propetamphos in mg/m²*

| | | | | |
|---|---|---|---|---|
| 250 ml/100 m² @ | 4.0% = | 100 to 124 = | 250 ml/100 m² @ | 4.96% |
| 500 ml/100 m² @ | 2.0% = | 100 to 124 | 500 ml/100 m² @ | 2.48% |
| 750 ml/100 m² @ | 1.33% = | 100 to 124 = | 750 ml/100 m² @ | 1.65% |
| 1000 ml/100 m² @ | 1.0% = | 100 to 124 = | 1000 ml/100 m² @ | 1.24% |

Emulsifiable Concentrates Final Dilution:

*Ranges of Propetamphos in mg/m²*

| | | | | |
|---|---|---|---|---|
| 500 ml/100 m² @ | 1.04% = | 52 to 224 = | 500 ml/100 m² @ | 4.48% |
| 1000 ml/100 m² @ | 0.52% = | 52 to 224 = | 1000 ml/100 m² @ | 2.24% |
| 1500 ml/100 m² @ | 0.35% = | 52 to 224 = | 1500 ml/100 m² @ | 1.49% |
| 2000 ml/100 m² @ | 0.26% = | 52 to 224 | 2000 ml/100 m² @ | 1.12% |

*Preferred of Propetamphos in mg/m²*

| | | | | |
|---|---|---|---|---|
| 500 ml/100 m² @ | 1.52% = | 76 to 148 = | 500 ml/100 m² @ | 2.96% |
| 1000 ml/100 m² @ | 0.76% = | 76 to 148 = | 1000 ml/100 m² @ | 1.48% |

TABLE C-continued

W:W Formulation Adjustments in Propetamphos mg/m²

| | | | | |
|---|---|---|---|---|
| 1500 ml/100 m² @ | 0.51% = | 76 to 148 | 1500 ml/100 m² @ | 0.99% |
| 2000 ml/100 m² @ | 0.38% = | 76 to 148 | 2000 ml/100 m² @ | 0.74% |

Most preferred Ranges of Propetamphos in mg/m²

| | | | | |
|---|---|---|---|---|
| 500 ml/100 m² @ | 2.0% = | 100 to 124 | 500 ml/100 m² @ | 2.48% |
| 1000 ml/100 m² @ | 1.0% = | 100 to 124 | 1000 ml/100 m² @ | 1.24% |
| 1500 ml/100 m² @ | 0.67% = | 100 to 124 | 1500 ml/100 m² @ | 0.83% |
| 2000 ml/100 m² @ | 0.5% = | 100 to 124 | 2000 ml/100 m² @ | 0.62% |

The mixture of both active ingredients (propetamphos and hydroprene) is administered through any acceptable mode of the application of pesticides such as spraying, fogging, dusting, painting, spreading, etc.; however, the administration in the form of a propetamphos emulsifiable concentrate mixed with the hydroprene concentrate is preferred.

Whatever is the means of administration of the mixture, both propetamphos and hydroprene are tank mixed together and dispensed at 500 ml to 2000 ml per 100 m² for emulsifiable concentrates and 250 ml to 1000 ml per 100 m² for aerosols to achieve for (RS)-hydroprene 12 to 50 mg/m², preferably 18 to 36 mg/m², most preferably 20 to 30 mg/m² or for (S)-hydroprene 1 to 20 mg/m², preferably 2 to 15 mg/m², most preferably 3 to 13 mg/m² and for propetamphos 52 to 224 mg/m², preferably 76 to 148 mg/m² and most preferably 100 to 124 mg/m². Application is to the whole facility but particularly to cracks, crevices, and spots.

Hydroprene may be formulated either as a fogger, an emulsifiable concentrate or any other suitable formulation form. Specific examples of hydroprene formulations are illustrated in Example 1.

Propetamphos may be in the aqueous form, as an emulsifiable concentrate or in any other suitable formulation form. Specific examples of propetamphos formulations are illustrated in Example 1.

A mixture of propetamphos with hydroprene may be formulated as a ready-to-use formulation, an aerosol, an emulsifiable concentrate or a solid. These formulations are illustrated in Example 1.

One suitable method of preparing the (RS)-hydroprene/propetamphos mixture, or the (S)-hydroprene/propetamphos mixture is to blend concentrates of diluted propetamphos with a suitable carrier substance and then mix the resulting composition with technical or diluted (RS)- or (S)-hydroprene in a ratio of from 1:1 to 18.7:1 of propetamphos to (RS)-hydroprene or 2.6:1 to 224:1 of propetamphos to (S)-hydroprene, preferably in a ratio of from 3.3:1 to 6.2:1 of propetamphos to (RS)-hydroprene and from 7.7:1 to 41.3:1 of propetamphos to (S)-hydroprene.

The formulations of the present invention either individually or in the mixture may include conventional insect control formulation adjuvants, diluents, modifiers or conditioning agents, herein included in the term "suitable carrier substance" to provide formulations in the form of solutions, emulsions, dispersions, powders, dusts, granules and the like. Thus, the formulations of the present invention can be liquid or solid. The liquid formulations can contain one or more surface active agents as a conditioning agent to render the formulation readily dispersible in water or other liquid. The term "surface active agents" includes wetting agents, sticking agents, dispersing agents, emulsifying agents, and the like. The solid formulations of the present invention in the form of powder, dust or granules can be prepared using such substances as talc, natural clay, diatomaceous earth and silica, particularly finely divided silica such as Hi-Sil.

The amount of active ingredient in the formulations of the present invention will vary according to the formulation and the manner in which the formulation is to be applied but, in general, will be from about 0.1–20% for propetamphos and 0.01–10% for hydroprene. The ratio of propetamphos to (RS)-hydroprene is generally from about 1:1 to 18.7:1 by weight and for propetamphos to (S)-hydroprene from about 2.6:1 to 41.3:1 by weight.

The following examples are provided to illustrate how to practice the present invention. They should not be construed as narrowing or limiting its scope. In all examples, all parts and percentages are by weight unless otherwise specified.

EXAMPLE 1

Field Evaluations

Four types of insecticidal agents—hydroprene, propetamphos, dichlorvos and chlorpyrifos—and combinations thereof were tested individually or as a mixture in field trials for their effectiveness against cockroaches. In addition to the various insecticides, methods of application and the frequency of application, various formulations were also evaluated in this testing regime.

Methods

Cockroach Population Assessment
Testing Sites and Controls

Suitable apartment complexes for testing were located. To qualify for testing, each apartment complex had to have a certain degree of cockroach infestation.

Either a negative or positive control was maintained. If apartments were used in the test, the control units were in the same complex but separated so as to avoid migration. Complexes were ideally units in a single building on one side of a parking lot for the treated group and the same number of units of identical construction were on the other side of the parking lot for the control group.

Special care was taken to assure that the complexes were completely separated from each other, preferably with yard, parking lot or at least a driveway, to prevent the migration of cockroaches.

When a small town was used for the testing, the treated apartments or houses were separated by a main road from those used as controls.

Qualifications for Testing Requirements

To qualify as a test site, a minimum pretreatment count of 15 cockroaches daily per three traps was required. If, using this criteria, the majority of the apartments in one complex qualified, all the apartments in the complex were used for testing of one type of insecticidal agent. The total number of pre-treatment cockroaches trapped in the complex were counted within the month prior to treatment and such counting was repeated monthly during the treatment up to the end. Then, each testing period was expressed as the average percent reduction over all the apartments in a complex treated with one agent.

Once the apartment complexes qualified, the random assignment to treat each complex with a different agent was made and a letter to that effect was sent out to all tenants to explain what would be done at their apartments.

Monitoring Methods

Each test site was monitored within at least one month prior to treatment to establish a pre-treatment level of cockroach infestation. For the determination of pretreatment level of infestation the trap count monitoring method was preferred. In some instances, the trap count was supplemented by visual count.

Controls were monitored identically to the treated groups.

Trap counts

In most instances, three sticky cockroach traps (usually Black Flag Roach Motel ®) with attractant were placed in the apartment in areas of apparent heaviest infestation. The three traps were placed in the kitchen of each apartment for 24 hours. The trap locations were as follows: (1) on the counter near the sink, (2) in the cabinet underneath the sink, and (3) on the floor near the range or the refrigerator. The same locations of these traps were monitored monthly up to twelve months. Individual trap counts were made for each apartment over the entire study. If only one or two traps were used to determine pretreatment infestation levels, then throughout the whole study only that location was monitored. After 24 hours of monitoring, the traps were collected and brought back to the laboratory for counting.

The traps were left out for 24 hours, then collected, and cockroaches were counted as normal adults, IGR adults and nymphs. The raw data were then recalculated for percent of reduction using the following formula:

$$\frac{T_o - T_i}{T_o} \times 100 = \text{Percent Reduction}$$

$T_o$ = pretreatment count
$T_i$ = posttreatment count at the time i

Interpretation of Data

The cockroach counts were recorded as:
total numbers of cockroaches per testing site;
total normal adults per testing site;
total IGR affected adults;
total immatures per testing site.

Obtained data were expressed in the following Tables 2-14 as the percent of reduction (R%) of pretreatment count; the percent of juvenile hormone affected adults (IGR) comparing with normal adults only; the percent of adults (A) in the total population and the percent of nymphs (N) in the total population.

Visual counts

Some areas of primary harborage, particularly that of breeding ground, were visually inspected and counts of the cockroaches were logged for the month prior to the testing period. The same areas were monitored throughout the whole testing period, i.e. up to nine months following the application of the tested formulation.

Testing Materials

A. Propetamphos

The solution of propetamphos applied to designated apartment complexes was prepared from 50% propetamphos emulsifiable concentrate (EC) diluted with water to produce 1.0% solution. The 1.0% solution was applied with low pressure compressed air hand sprayer either as a spot, crack and crevice treatment or as a general space treatment according to the label instructions.

50% propetamphos EC was prepared as tank mix from the following formulating agents:

| Propetamphos-50% Emulsifiable Concentrate (EC) | | |
|---|---|---|
| Ingredients | (w/w %) | Source |
| Propetamphos Technical (90%) | 56.11 | Sandoz |
| Cellosolve ® (ethylene glycol ethyl ether) | 38.89 | Union Carbide |
| Sponto ® N-140-B (emulsifier) | 5.00 | Witco |

B. Hydroprene

The hydroprene applied to designated apartment complexes was supplied in the following formulations:

| (RS) -Hydroprene - 65.7% Emulsifiable Concentrate (EC) | | |
|---|---|---|
| Ingredients | (w/w) % | Source |
| (RS) -Hydroprene Technical (90%) | 74.56 | Zoecon |
| Igepal ®CO-630 (surfactant) | 25.44 | GAF |

65.7% hydroprene EC is suitable for dilution with water.

| 0.6% (RS) -Hydroprene Fogger Concentrate A | | |
|---|---|---|
| Ingredients | (w/w)% | Source |
| (RS) -Hydroprene (95.03%) | 0.66 | Zoecon |
| methylene chloride (inhibited aerosol grade solvent) | 16.34 | Commodity |
| 1,1,1-trichloroethane (inhibited aerosol grade solvent) | 55.00 | Commodity |

| 0.6% (RS) -Hydroprene Fogger Concentrate B | | |
|---|---|---|
| Ingredients | (w/w) % | Source |
| (RS)-hydroprene (95.03%) | 0.89 | Zoecon |
| Methylene chloride (inhibited aerosol grade solvent) | 22.72 | Dow |
| 1,1,1-trichloroethane (inhibited aerosol grade solvent) | 76.39 | Dow |

| 0.6% (RS) -Hydroprene Fogger A | | |
|---|---|---|
| Ingredients | (w/w) % | Source |
| 15% Hydroprene Manufacturing Conc.* | 4.81 | Zoecon |
| Methylene Chloride (inhibited aerosol grade solvent) | 12.91 | Dow |
| 1,1,1-trichloroethane (inhibited aerosol grade solvent) | 55.0 | Dow |
| Propellant A-70 | 28.0 | Commodity |

| 0.6% (RS) -Hydroprene Fogger B | | |
|---|---|---|
| Ingredients | W/W % | Source |
| 0.6% (RS) -hydroprene fogger concentrate B | 72.0 | Zoecon |

-continued

| Ingredients | (w/w) % | Source |
|---|---|---|
| Propellant A-70 (Hydrocarbon Propellant) | 28.0 | Commodity |

1.2% (RS)-Hydroprene Fogger Concentrate A

| Ingredients | (w/w) % | Source |
|---|---|---|
| (RS)-Hydroprene (95.03%) | 1.28 | Zoecon |
| Aerothene ® MM | 15.72 | Commodity |
| Aerothene ® TT | 55.00 | Commodity |

1.2% (RS)-Hydroprene Fogger Concentrate B

| Ingredients | W/W % | Source |
|---|---|---|
| (RS)-hydroprene (95.03%) | 1.8 | Zoecon |
| Methylene Chloride (inhibited aerosol grade solvent) | 21.8 | Dow |
| 1,1,1-trichloroethane (inhibited aerosol grade solvent) | 76.4 | Dow |

1.2% (RS)-Hydroprene Fogger

| Ingredients | (w/w) % | Source |
|---|---|---|
| 1.2% (RS)-Hydroprene fogger concentrate | 72 | Zoecon |
| A-70 propellant | 28 | Commodity |

0.6% (RS)-Hydroprene Aerosol 0.6% (RS)-hydroprene aerosols are prepared as 0.6% (RS)-hydroprene foggers and fitted with 0.020 in. MBST #01-5018 aerosol actuators rather than fogger actuators.

9.0% (S)-Hydroprene Emulsifiable Concentrate

| Ingredients | W/W % | Source |
|---|---|---|
| (S)-Hydroprene Technical (91.0%) | 10.09 | Zoecon |
| Tenox 4 [1] Antioxidant | 0.50 | Eastman |
| Atlox 847 [2] Emulsifier | 19.03 | I.C.I. |
| Atlox 3404F [3] Emulsifier | 11.42 | I.C.I. |
| Isopar M [4] Solvent | 58.96 | Exxon |

[1] Antioxidant - Corn oil solution of BHT (Butylated hydroxytoluene) and BHA (butylated hydroxyanisole).
[2] Emulsifier: Alkoxylated polyol fatty acid ester.
[3] Emulsifier: Proprietary blend of nonionic and ionic emulsifiers
[4] Solvent: Isoparaffinic solvent

0.3% (S)-Hydroprene Fogger

| Ingredients | W/W % | Source |
|---|---|---|
| (S)-hydroprene Technical (91.0%) | 0.40 | Zoecon |
| Methylene Chloride (inhibited aerosol grade solvent) | 16.55 | Dow |
| 1,1,1-trichloroethane (inhibited aerosol grade solvent) | 55.00 | Dow |
| Propellant A-70 (hydrocarbon propellant) | 28.00 | Commodity |
| BHT-Antioxidant (butylated hydroxytoluene) | 0.05 | Eastman |

0.3% (S)-Hydroprene Aerosol 0.3% (S)-hydroprene aerosols are prepared as are the 0.3% (S)-hydroprene foggers except the actuators are suited to hand held aerosol delivery.

C. Chlorpyrifos
Dursban ® EC 0.25% was purchased from DOW Chemical Company.
D. Dichlorvos
Vapona ® EC 0.25% (DDVP) was obtained from Shell Co.

*The hydroprene manufacturing concentrate is a dilution of technical hydroprene in methylene chloride at the 15% level.

E. Hydroprene/Propetamphos Mixtures
1. Tank mixes
Hydroprene/propetamphos formulations were prepared by mixing 65.7% hydroprene EC with 50% propetamphos EC together in a tank of water just prior to use. The final EC tank mixture was applied according to instructions on the propetamphos label for application of propetamphos.
2. Combination Formulations

59.7% Propetamphos/7.2% (RS)-Hydroprene EC Formulation

| Ingredients | W/W % | Source |
|---|---|---|
| Propetamphos technical (90%) | 76.2 | Sandoz |
| (RS)-Hydroprene technical (94%) | 6.5 | Zoecon |
| Tenox ® 4 (anitoxidant) | 0.7 | Eastman |
| Atlox ® 3406F (emulsifier) | 11.6 | ICI |
| Atlox ® 3409 (emulsifier) | 5.0 | ICI |

This formulation in particular is preferred for applications to crack and crevice areas of the locus.

Propetamphos/(RS)-Hydroprene Aerosol Formulation (Fogger)

| Ingredients | W/W % | Source |
|---|---|---|
| Propetamphos technical (90%) | 1.20 | Sandoz |
| (RS)-Hydroprene (manufacturing concentrate 15%) | 4.81 | Zoecon |
| methylene chloride | 10.99 | Dow |
| 1,1,1-trichloroethane | 55.00 | Dow |
| A-46 propellant | 25.00 | Commodity |

The above formulation in particular is preferred for applications to crack and crevice areas of the locus.

| Ingredient | W/W % | Source |
|---|---|---|
| Propetamphos/(RS)-Hydroprene Solid Formulation | | |
| Propetamphos (technical 90%) | 1.33 | Sandoz |
| (RS)-Hydroprene (technical 88%) | 0.14 | Zoecon |
| Barden ® AG-1 (aluminum silicate) | 88.53 | Commodity |
| Hi-Sil ® 233 (silica) | 5.00 | Commodity |
| Ethylene glycol | 5.00 | Commodity |
| Ready to Use Formula - Propetamphos/(RS)-Hydroprene | | |
| Propetamphos Tech. (90%) | 1.23 | Sandoz |
| (RS)-Hydroprene Technical (90%) | 0.36 | Zoecon |
| Sponto ® AK 31-568 | 0.40 | Witco |
| Sponto ® AK 31-56A | 1.60 | Witco |
| Water | 94.58 | Commodity |
| Xylene Range Aromatic Solvent | 1.00 | Commodity |
| BHT | 0.44 | Commodity |
| Colloid 643 | 0.02 | Commodity |
| Tetrasodium EDTA | 0.2 | Commodity |
| Citric Acid | 0.1 | Commodity |
| Dowicil ® 75 (stabilizer) | 0.07 | Dow |
| 3.6% (S)-Hydroprene/59.7% Propetamphos EC | | |
| Propetamphos Tech. (89%) | 68.42 | Sandoz |
| (S)-hydroprene Tech. (91%) | 4.75 | Zoecon |
| BHT Antioxidant (butylated hydroxytoluene) | 5.00 | Eastman |
| Atlox 3406F-XF (proprietary blend of emulsifiers) | 15.27 | ICI |
| Atlox 3409 F-XF (proprietary blend of emulsifiers) | 6.56 | ICI |

In individual use the hydroprene foggers were 5 oz. cans applied at a rate of 250 ml/100 m$^2$ of area to be treated. The percentage of (RS)-hydroprene in the foggers was either 1.2% or 0.6% and of (S)-hydroprene, 0.3%. At least one fogger was placed in the kitchen and bathroom of each unit, with the remaining foggers (if any) being placed throughout the unit as needed. All cabinets and drawers were cleaned out and left open so the fog would cover as much area as possible.

The (RS)-hydroprene aerosol was a 5 oz. can of 0.6% a.i. Aerosol was applied to cabinets, drawers, under appliances, and any other possible cockroach harborage in the kitchen and bathroom.

Trap counts were taken at monthly intervals throughout the test, in the same manner as pre-treatment counts. In some studies, re-application of the hydroprene and/or propetamphos was done at either 3, 4, or 6 months after the initial application. The percent reduction was calculated using the formula disclosed herein in Roach Population Assessment. These tests ran for a period of up to 11 months.

Table 1 illustrates the effect of application of propetamphos alone, (RS)-hydroprene alone, and the mixture of both in various formulations on the German cockroach (*Blatella germanica*) population in the cockroach infested facilities up to nine months. For determination of efficacy, post-treatment counts were compared to pretreatment counts and expressed in percent of the reduction or increase of the number of cockroaches. The initial pretreatment count of cockroaches equals to 0% reduction.

In the following examples and tables, formulations used were as follows:

"H/P Mixture" is a tank mix of a 1.0% solution from 50% propetamphos EC, a 0.12% solution from 65.7% (RS)-hydroprene EC, and water.

"H/P Combination" is a combination treatment using 0.6% (RS)-hydroprene fogger and a 1% solution from 50% propetamphos EC.

"(RS)-hydroprene 0.12% EC" is a 0.12% solution from 65.7% (RS)-hydroprene EC in water.

"Propetamphos 1.0% EC" is a 1.0% solution from 50% propetamphos EC in water.

TABLE 1

| No. Apt. | (RS) Hydroprene EC 0.12% (20) | (RS) Hydroprene Fogger (16) | Propetamphos EC 1% (19) | H/P Mixture EC 0.12/1% (15) | H/P Combination H-Fogger/P-EC (16) |
|---|---|---|---|---|---|
| Months | | | | | |
| 0 | 0% | 0% | 0% | 0% | 0% |
| 1 | −69% | −33% | 53% | 78% | 89% |
| 2 | −77% | 21% | 80% | 75% | 94% |
| 3 | −18% | — | 78% | 80% | 97%R |
| 4 | −56% | — | 61%R | 88%R | 95% |
| 5 | term | — | 67% | 90% | 96% |
| 6 | | 71% | 22% | 95% | 97% |
| 7 | | term | term | — | — |
| 8 | | | | 94% | 97% |
| 9 | | | | 99% | 100% |

R = retreatment with the same agent

Table 1 shows that in reducing the cockroach population, the mixture of propetamphos and (RS)-hydroprene in emulsifiable concentrate forms (H/P mixture) and the combination of (RS)-hydroprene fogger and propetamphos emulsifiable concentrate (H/P Combination) are highly superior to the treatment with propetamphos alone or (RS)-hydroprene alone. The residual and toxic activity of the H/P Mixture and of the H/P Combination were extended. In addition, 89% of the surviving adult cockroaches at 4 months following the application of the H/P Mixture were "IGR adults", i.e. abnormal and infertile cockroaches.

Treatment with propetamphos alone resulted in supression of 80% of the cockroach population by the second month but from the third months on such reduction slowly ceased and at 6 months the reduction caused by propetamphos alone was only 22% against the original number of cockroaches. Remaining surviving normal adult cockroaches were at all times capable of reproducing and hence able to restore the population within the short time after the residual levels decreased to the pretreatment levels.

Treatment of a cockroach population by (RS)-hydroprene EC alone actually increased the population of cockroaches by approximately 56% in four to six months following treatment. Nevertheless, these cockroaches were all IGR abnormal adults and were therefore unable to reproduce.

EXAMPLE 2

Field tests were conducted in heavily infested low income housing units located in Indianapolis. The purpose of these tests was to determine relative efficacy, residual life and effective concentration of (RS)-hydroprene alone and (RS)-hydroprene in combination with known insecticides chloropyrifos (Dursban ®) and dichlorvos (Vapona ®) and to compare the results with untreated controls and with the effect of insecticide alone.

Table 2 illustrates the trap catch reduction of all stages.

TABLE 2

| Treatment | % Reduction of Roaches at Indicated Time Posttreatment | | | | | |
|---|---|---|---|---|---|---|
| | 2 wk | 1 mo | 2 mo | 3 mo | 6 mo | 1 year |
| (RS)-Hydroprene 1.2% fogger | −4.6 | −32.5 | 20.8 | — | 71.1 | 53.4 |
| (RS)-Hydroprene 5.67 ml/gal spray | 2.3 | −20.4 | −18.6 | — | 73.8 | 46.8 |
| (RS)-Hydroprene Spray/Dursban /Vapona Spray | | 38.4 | 29.1 | 53.0 | — | 47.4 |
| Dursban/Vapona Spray | 48.5 | 65.7 | 79.7 | 70.0 | −28.7 | −7.8 |
| Control Untreated | 15.2 | 2.8 | — | | 47.5 | 37.1 |

Treatment with (RS)-hydroprene alone gave the best results only at six months period and such effect persisted as long as one year. The two insecticides chlorpyrifos and dichlorvos provided reasonably good control up to three months but after that their effect disappeared and at six months the cockroach population was actually higher in insecticide-treated apartments than it was before the treatment.

Table 3 illustrated the trap catch reduction of adult cockroaches.

TABLE 3

| Treatment | % Reduction of Adults at Indicated Time Posttreatment | | | | | |
|---|---|---|---|---|---|---|
| | 2 wk | 1 mo | 2 mo | 3 mo | 6 mo | 1 year |
| (RS)-Hydroprene 1.2% fogger | | −5.0 | −0.4 | 11.8 | — | 61.6 |
| (RS)-Hydroprene | 9.6 | −4.0 | −26.3 | — | 75.4 | — |

TABLE 3-continued

| Treatment | % Reduction of Adults at Indicated Time Posttreatment | | | | | |
|---|---|---|---|---|---|---|
| | 2 wk | 1 mo | 2 mo | 3 mo | 6 mo | 1 year |
| 5.67 ml/gal spray (RS)-Hydroprene Spray/Dursban /Vapona Spray | | 21.1 | 8.6 | 43.0 | — | 33.0 |
| Dursban/Vapona Spray | 19.3 | 46.7 | 80.4 | 79.9 | −49.4 | — |
| Control Untreated | 5.3 | −8.2 | | — | 35.2 | — |

Table 4 illustrated the trap catch reduction of nymphal cockroaches.

TABLE 4

| Treatment | % Reduction of Nymphs at Indicated Time Posttreatment | | | | | |
|---|---|---|---|---|---|---|
| | 2 wk | 1 mo | 2 mo | 3 mo | 6 mo | 1 year |
| (RS)-Hydroprene 1.2% fogger | | −17.1 | −47.1 | 25.0 | — | 77.2 |
| (RS)-Hydroprene 5.67 ml/gal spray | −1.5 | −28.4 | 14.33 | — | 72.8 | — |
| (RS)-Hydroprene Spray/Dursban /Vapona Spray | | 44.9 | 37.5 | 57.1 | — | 52.7 |
| Dursban/Vapona Spray | 60.9 | 45.5 | 19.6 | — | 54.4 | — |
| Control Untreated | 19.1 | 7.22 | | — | 52.3 | — |

EXAMPLE 3

Results obtained from other individual field testing are illustrated in Tables 5-14. %R=percent reduction of pretreatment count IGR=percent of juvenile hormone affected adults as compared with normal adults only N=percent of nymphs in the total population. A=percent of adults in the total population. A. The Fairfield Inn Apartments were treated with 1 2% (RS)-hydroprene fogger, 0.6% (RS)-hydroprene aerosol, and 1% propetamphos EC. Thirty-four apartments total were treated. Results are given in Table 5.

TABLE 5

| Fairfield Apartments | | | |
|---|---|---|---|
| Pre-Treat Counts | | | |
| Initial | 986 | | |
| | Post-Treatment % Reduction | | |
| | % R | IGR | N |
| 0 Months | 0 | 0 | 64 |
| 1 Month | 71 | 52 | 50 |
| 2 Month | 78 | 84 | 43 |
| 3 Month | 86 | 77 | 34 |
| 4 Month | 91 | 93 | 37 |
| 5 Month | 95 | 92 | 27 |
| 6 Month | 90 | 93 | 26 |
| 7 Month | — | — | — |
| 8 Month | 94 | 93 | 22 |
| 9 Month | — | — | — |
| 10 Month | — | — | — |
| 11 Month | 100 | 0 | 100 |

B. The Willows Apartments were treated with 0 6% (RS)-hydroprene fogger, 0.6% (RS)-hydroprene aerosol, and 1% propetamphos EC. The hydroprene treatment was repeated at four months after the initial treatment. The aerosol was sprayed around the kitchen area, in the bathroom and in the closet in these types of units. Then a single fogger was placed in the center of the room. Propetamphos was applied as a spot treatment. Twenty-four apartments were treated. Results are given in Table 6.

TABLE 6

| Willows Apartments | | | |
|---|---|---|---|
| Pre-Treat Counts | | | |
| Initial | 885 | | |
| | Post-Treatment % Reduction | | |
| | % R | IGR | N |
| 0 Months | 0 | 0 | 0 |
| 1 Month | 59 | 48 | 69 |
| 2 Month | 72 | 80 | 55 |
| 3 Month | 82 | 81 | 50 |
| 4 Month | 85 | 87 | 45 |
| 5 Month | 92 | 89 | 40 |
| 6 Month | 95 | 97 | 28 |
| 7 Month | — | — | — |
| 8 Month | 98 | 83 | 14 |
| 11 Month | 99 | 75 | 0 |

C. The Northwood Apartments are government subsidized units from two to four bedrooms with one or two baths. A group of 20 apartments was used to evaluate the effects of a 1.0% propetamphos E.C. treatment without any (RS)-hydroprene. This application was made per label directions using an average of 1 quart solution per apartment. The highest percent reduction was at 2 months with 80%, at which point it dropped until a re-treatment at 4 months. The level of control never reached as high as the various (RS)-hydroprene/propetamphos treatments. The propetamphos units were dropped from testing at month 9 and re-treated with hydroprene and propetamphos. The last treatment at the Northwood apartments was a 0.12% (RS)-hydroprene E.C. tank mixed with a 1.0% propetamphos E.C. and applied according to the propetamphos label. A 1 gallon B & G compressed air sprayer was used for this treatment as well as for the propetamphos E.C. applications. This treatment provided fairly good control initially and with a 4 month re-treatment gave 99% reduction by the ninth month. Number of apartments included in each treatment is in parenthesis.

TABLE 7

| Northwood Apartments (20) Propetamphos 1% EC | | | |
|---|---|---|---|
| Pre-Treat Counts | | | |
| Initial | 290 | | |
| | Post-Treatment % Reduction | | |
| | % R | IGR | N |
| 0 Month | 0 | 0 | 0 |
| 1 Month | 53 | 1 | 45 |
| 2 Month | 80 | 0 | 50 |
| 3 Month | 78 | 10 | 67 |
| 4 Month | 61 | 7 | 60 |
| 5 Month | 67 | 2 | 57 |
| 6 Month | 22 | 7 | 70 |
| 8 Month | 77 | 17 | 66 |

TABLE 8

| Northwood Apartments (18) (RS)-Hydroprene 0.6% Fogger and 0.6% aerosol; Propetamphos 1% EC | | | |
|---|---|---|---|
| Pre-Treat Counts | | | |
| Initial | 641 | | |
| | Post-Treatment % Reduction | | |
| | % R | IGR | N |
| 0 Month | 0 | 0 | 0 |
| 1 Month | 91 | 56 | 34 |
| 2 Month | 96 | 71 | 26 |
| 3 Month | 97 | 64 | 22 |

TABLE 8-continued

Northwood Apartments (18)
(RS)-Hydroprene 0.6% Fogger and 0.6% aerosol;
Propetamphos 1% EC

| | | | |
|---|---|---|---|
| 4 Month | 99 | 75 | 50 |
| 5 Month | 99 | 33 | 40 |
| 6 Month | 98 | 14 | 50 |
| 7 Month | — | — | — |
| 8 Month | 99 | 50 | 0 |
| 9 Month | 100 | 100 | 0 |

TABLE 9

Northwood Apartments (16)
(RS)-Hydroprene 0.6% aerosol;
Propetamphos 1% EC

| Pre-Treat Counts | | | |
|---|---|---|---|
| Initial | 773 | | |
| | Post-Treatment % Reduction | | |
| | % R | IGR | N |
| 0 Month | 0 | 0 | 0 |
| 1 Month | 88 | 68 | 38 |
| 2 Month | 88 | 75 | 46 |
| 3 Month | 84 | 83 | 47 |
| 4 Month | 82 | 83 | 53 |
| 5 Month | 87 | 96 | 54 |
| 6 Month | 90 | 85 | 29 |
| 8 Month | 96 | 80 | 11 |
| 9 Month | 99 | 100 | 33 |

TABLE 10

Northwood Apartments (16)
(RS)-Hydroprene 0.6% fogger;
Propetamphos 1% EC

| Pre-Treat Counts | | | |
|---|---|---|---|
| Initial | 593 | | |
| | Post-Treatment % Reduction | | |
| | % R | IGR | N |
| 0 Month | 0 | 0 | 0 |
| 1 Month | 89 | 44 | 43 |
| 2 Month | 94 | 64 | 35 |
| 3 Month | 97 | 58 | 25 |
| 4 Month | 95 | 79 | 32 |
| 5 Month | 96 | 59 | 26 |
| 6 Month | 97 | 67 | 37 |
| 7 Month | — | — | — |
| 8 Month | 97 | 50 | 48 |
| 9 Month | 100 | 100 | 50 |

TABLE 11

Northwood Apartments (16)
0.12% (RS)-Hydroprene 5E;
1% Propetamphos EC (Tank Mix)

| Pre-Treat Counts | | | |
|---|---|---|---|
| Initial | 1004 | | |
| | Post-Treatmet % Reduction | | |
| | % R | IGR | N |
| 0 Month | 0 | 0 | 0 |
| 1 Month | 78 | 51 | 42 |
| 2 Month | 75 | 58 | 47 |
| 3 Month | 80 | 94 | 36 |
| 4 Month | 88 | 89 | 19 |
| 5 Month | 90 | 94 | 8 |
| 6 Month | 95 | 95 | 15 |
| 8 Month | 94 | 83 | 21 |
| 9 Month | 99 | 83 | 25 |

D. One half of the Chateau apartment were treated with Mr. Scott's® 0.5% ready-to-use chlorpyrifos (Table 13). In the second half of the apartments 0.6% (RS)-hydroprene fogger at 250 ml/100 m² and 0.6% 5 oz. (RS)-hydroprene aerosol for the kitchen and bathroom were used (Table 12).

The results show an increase in both test populations, with the (RS)-hydroprene treated apartment increasing at a slower rate. After the six month data point the chlorpyrifos treatment was terminated for various reasons and apartment were dropped from the test and retreated with hydroprene and propetamphos. Ten apartments were treated in each test.

TABLE 12

Chateau Apartments
(RS)-Hydroprene 0.6% fogger and 0.6% aerosol;
Chlorpyrifos 0.5%

| Pre-Treat Counts | | | |
|---|---|---|---|
| Initial | 127 | | |
| | Post-Treatment % Reduction | | |
| | % R | IGR | N |
| 0 Month | 0 | 0 | 0 |
| 1 Month | −218 | 58 | 65 |
| 2 Month | −172 | 71 | 72 |
| 3 Month | −164 | 69 | 65 |
| 4 Month | — | — | — |
| 5 Month | — | — | — |
| 6 Month | −87 | 26 | 52 |

TABLE 13

Chateau Apartments
Chlorpyrifos 0.5%

| Pre-Treat Counts | | | |
|---|---|---|---|
| Initial | 103 | 0 | 72 |
| | Post-Treatment % Reduction | | |
| | % R | IGR | N |
| 0 Month | 0 | 0 | 0 |
| 1 Month | −242 | 36 | 73 |
| 2 Month | −561 | 45 | 73 |
| 3 Month | −451 | 57 | 72 |
| 4 Month | — | — | — |
| 5 Month | — | — | — |
| 6 Month | −287 | 17 | 65 |

EXAMPLE 4

In a similar manner and following the procedures of Examples 1 through 3, two buildings of the Whitsonian Apartments were treated as follows.

Buildings 1 (13 units) and 5 (8 units) were treated with 59.7% propetamphos/7.2% (RS)-hydroprene EC at initial treatment.

Building 1 was re-treated at 6 months with 59.7% propetamphos/7.2% (RS)-hydroprene EC.

Building 5 was re-treated at 6 months with 59.7% propetamphos/3.6% (S)-hydroprene EC.

The results in Table 14 show excellent and continuing reduction of the cockroach population through ten months, with the population in the (S)-hydroprene-treated apartments completely eradicated at nine months.

TABLE 14

Whitsonian Apartments

| | Building 1 | | | Building 5 | | |
|---|---|---|---|---|---|---|
| Pre-treatment counts | 999 | | | 252 | | |
| | Post-Treatment % Reduction | | | | | |
| | % R | IGR | % N | % R | IGR | % N |
| 0 Month | 0 | 0 | 69 | 0 | 0 | 54 |
| 2 Month | 46 | 67 | 48 | 55 | 73 | 54 |
| 3 Month | 58 | 62 | 29 | 55 | 83 | 39 |
| 4 Month | 80 | 79 | 31 | 84 | 83 | 44 |

TABLE 14-continued

| Whitsonian Apartments | | | | | | |
|---|---|---|---|---|---|---|
| | Building 1 | | | Building 5 | | |
| Retreat at 6 Months | | | | | | |
| 7 Month | 86 | 39 | 45 | 98 | 20 | 17 |
| 8 Month | 89 | 56 | 47 | 98 | 50 | 60 |
| 9 Month | 93 | 56 | 49 | 100 | 0 | 0 |
| 10 Month | 95 | 59 | 27 | 100 | 0 | 0 |

EXAMPLE 5

In a similar manner and following the procedures of Examples 1 through 3, the spot treatment with 1% propetamphos EC is followed with general space treatment using any one of hydroprene EC, hydroprene 0.6% fogger concentrate, hydroprene 0.6% fogger, hydroprene 1.2% fogger concentrate, hydroprene 1.2% fogger and hydroprene 0.6% aerosol for control of cockroach population.

All formulations used in this example are disclosed in Example 1 in details.

EXAMPLE 6

In a similar manner and following the procedures of Examples 1 through 3, the general space treatment with 1% propetamphos EC is followed with general space treatment using any one of hydroprene EC, hydroprene 0.6% fogger concentrate, hydroprene 0.6% fogger, hydroprene 1.2% fogger concentrate, hydroprene 1.2% fogger and hydroprene 0.6% aerosol is used for control of cockroach population.

All formulations used in this example are disclosed in Example 1 in details.

What is claimed is:

1. A method for the control of a cockroach population which method comprises applying to the locus of the cockroach infestation a synergistic effective amount of propetamphos in an amount of from 52–224 mg/m$^2$ and hydroprene in an amount of from 1 to 50 mg/m$^2$.

2. A method according to claim 1 wherein (R,S)-hydroprene is employed in an amount of from 12 to 50 mg/m$^2$.

3. A method according to claim 2 wherein (S)-hydroprene is employed in an amount of from 1 to 20 mg/m$^2$.

4. A method according to claim 1 wherein propetamphos is employed in an amount of from 76 to 148 mg/m$^2$.

5. A method according to claim 2 wherein propetamphos is employed in an amount of from 76 to 148 mg/m$^2$.

6. A method according to claim 3 wherein propetamphos is employed in an amount of from 76 to 148 mg/m$^2$.

7. A method according to claim 5 wherein (R,S)-hydroprene is employed in an amount of from 18 to 36 mg/m$^2$.

8. A method according to claim 6 wherein (S)-hydroprene is employed in an amount of from 2 to 15 mg/m$^2$.

9. A method according to claim 1 wherein the method is employed to control actual cockroach infestation.

10. A method according to claim 1 wherein the method is used prophylactically.

11. A method according to claim 1 wherein propetamphos and hydroprene are co-applied in the form of a composition with a suitable carrier substance.

12. A method according to claim 1 wherein propetamphos and hydroprene are applied individually.

13. An insecticidal composition comprising a synergistic effective amount of propetamphos and hydroprene in the ratio of between 1:1 and 224:1 together with a suitable carrier.

14. A composition according to claim 13 wherein the hydroprene is in racemic form.

15. A composition according to claim 14 wherein the weight ratio of propetamphos:(R,S)-hydroprene is from 1:1 to 18.7:1.

16. A composition according to claim 15 wherein the weight ratio of propetamphos:(R,S)-hydroprene is from 3.3:1 to 6.2:1.

17. A composition according to claim 13 wherein the hydroprene is the (S) enantiomer.

18. A compound according to claim 17 wherein the weight ratio of propetamphos:(S)-hydroprene is from 2.6:1 to 224:1.

19. A compound according to claim 18 wherein the weight ratio of propetamphos:(S)-hydroprene is from 7.7:1 to 41.7:1.

* * * * *